United States Patent
Tomita et al.

[11] 3,984,693
[45] Oct. 5, 1976

[54] TOMOGRAPHIC APPARATUS

[75] Inventors: Chuji Tomita, Tokyo; Kazuo Kobayashi, Kashiwa; Tadayoshi Hamana; Yoshinori Takahashi, both of Tokyo, all of Japan

[73] Assignee: Hitachi Medical Corporation, Tokyo, Japan

[22] Filed: Sept. 2, 1975

[21] Appl. No.: 609,732

[52] U.S. Cl. ............................ 250/445 T; 250/320; 250/525
[51] Int. Cl.² ........................................ H01J 37/20
[58] Field of Search ............... 250/445 T, 320, 522, 250/523, 525

[56] References Cited
UNITED STATES PATENTS

| | | | |
|---|---|---|---|
| 2,167,115 | 7/1939 | Kieffer | 250/445 T |
| 3,082,321 | 3/1963 | Lego | 250/445 T |
| 3,139,526 | 6/1964 | Amand | 250/445 T |
| 3,770,955 | 11/1973 | Tomita et al. | 250/445 T |

*Primary Examiner*—Alfred E. Smith
*Assistant Examiner*—B. C. Anderson
*Attorney, Agent, or Firm*—Wenderoth, Lind & Ponack

[57] ABSTRACT

A tomographic apparatus in which an X-ray tube and a film travel in straight, circular, elliptical, near-hypocycloidal and spiral paths about a fixed point of an object, keeping a certain positional relationship between them. The X-ray tube and the film are supported by a link mechanism retaining the aforesaid positional relationship, and the above-mentioned movement is achieved by a control means. The control means comprises: a drive mechanism having an internal gear, and a planetary gear, in mesh with the internal gear, rotates itself and moves around the internal gear; and a control mechanism for controlling rotation of those gears.

8 Claims, 19 Drawing Figures

FIG.3
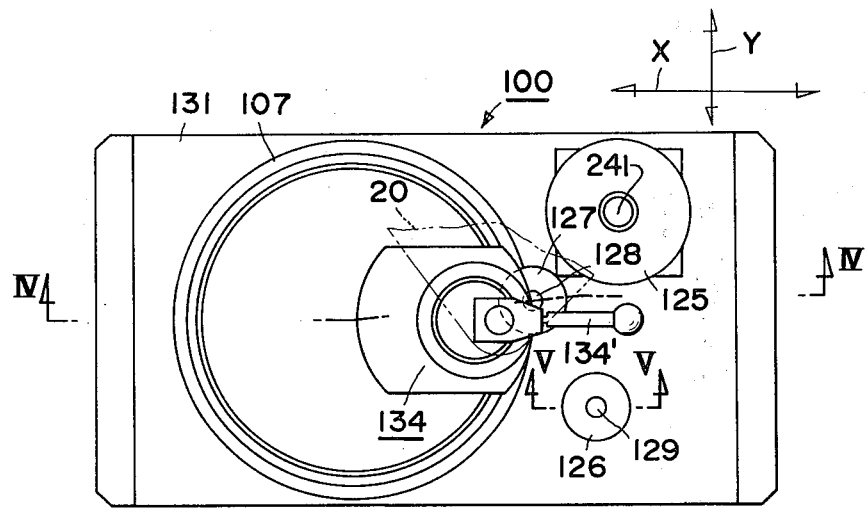
FIG.4
FIG.5
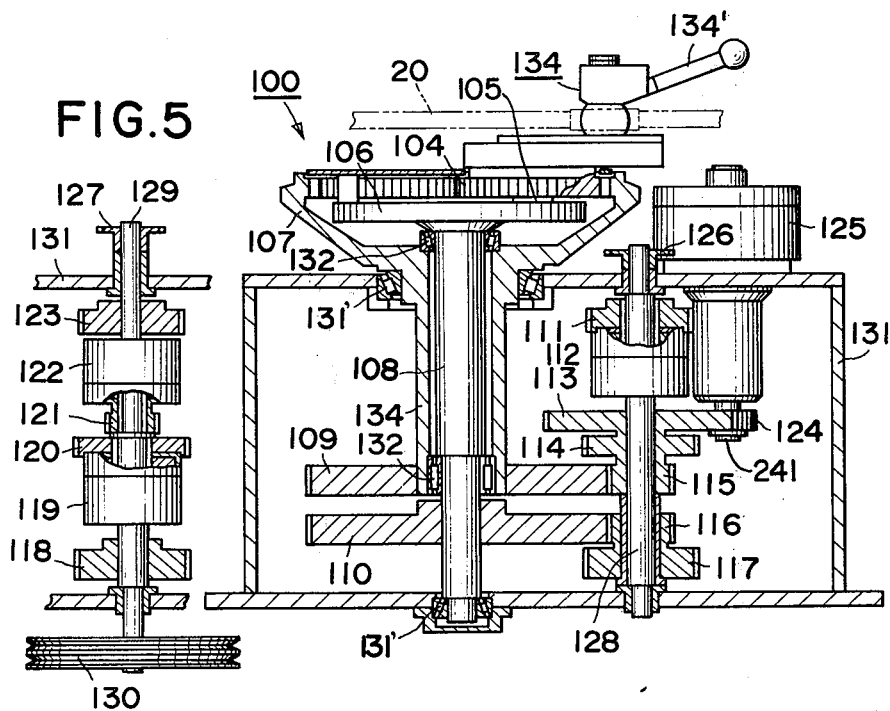

TOMOGRAPHIC APPARATUS

BACKGROUND OF THE INVENTION a. Field of the Invention:

The present invention relates to a tomographic apparatus.

b. Description of the prior art:

In general, a tomographic apparatus is intended to obtain tomograms of an object in which the required region is sharply imaged and the other parts are blurred, by moving an X-ray tube and a film about a certain point of the object while maintaining a certain positional relationship between them. From an ideal point of view, the X-ray tube and the film should at all times move in a path of movement best suited for an individual region of the object, but this is extremely difficult. In practice, most of paths of movement required are satisfied by a straight line, a circle, an ellipse, a hypocycloid and a spiral.

U.S. Pat. No. 3,770,955 discloses a tomographic apparatus capable of the aforesaid movement. In this apparatus, the X-ray and the film are supported by a link means which is driven by a cam-controlled hydraulic system. In this case, a highly trained operator is needed to handle such a hydraulic system.

On the other hand, mechanical means for controlling the movement of the X-ray tube and the film has been already disclosed in Japan patent application Publication Sho 38-1254 (publication date: Feb. 20, 1963), Japan Utility Model Laying-open Publication Sho 49-80,676 (laying-open date: July 12, 1974) and Japan Patent Laying-open Publication Sho 48-19,189 (laying-open date: Mar. 10, 1973). Those mechanical means fundamentally have an advantage of easy maneuvering, but a change or selection of the path of movement is still complicated and not substantially developed, as compared with the hydraulic means. At present, an apparatus of this kind is marketed under the tradename POLYTOME.

SUMMARY OF THE INVENTION

It is therefore an object of the present invention to provide an easy-to-handle tomographic apparatus which moves an X-ray tube and a film in straight, circular, elliptical, near-hypocycloidal and spiral paths about a fixed region of an object, keeping a positional relationship between them.

Another object of the present invention is to provide a tomographic apparatus which automatically moves the X-ray tube and the film in a selected path while the X-ray tube and the film lie in arbitrary positions.

Other objects of the present invention will be best understood by the following description and accompanying drawings.

BRIEF DESCRIPTION OF THE DRAWINGS

FIGS. 3 to 11 show control means for the tomographic apparatus in which:

FIGS. 3 to 5 show a drive mechanism for the control means, FIG. 3 being a plan view, FIG. 4 being a sectional view taken along line IV—IV in FIG. 3, and FIG. 5 being a sectional view taken along line V—V in FIG. 3;

FIGS. 6 and 7 show a control mechanism for the control means, FIG. 6 being a sectional view taken along line VI—VI in FIG. 7 which illustrates the bottom of the control mechanism with a part broken away;

FIGS. 8 and 9 show a pin-setting means provided in the drive mechanism, FIG. 8 being a plan view, FIG. 9 being a sectional view taken along line IX–IX in FIG. 8;

FIGS. 10A and 10B are perspective views of the control means with parts omitted for easy understanding; and FIG. 11 is an exploded view for illustrating types and forms of cam plates and a roller for a limit switch.

DETAILED DESCRIPTION OF THE PREFERRED EMBODIMENT

The following description will be directed to an embodiment according to the present invention by referring to the accompanying drawings.

In a tomographic apparatus of the present invention, movement of an X-ray tube and a film is determined by an internal gear and a planetary gear in mesh therewith. Such a mechanism is described in the Japan Patent Laying-open Publication Sho 48-19189. With a gear ratio of 2:1 of the internal gear to the planetary gear, when the internal gear and the planetary gear rotate, a first point on a pitch circle of the planetary gear and a second point at a position other than the first point in the planetary gear describe various paths of movement. When only the planetary gear, in engaging with the internal gear, rotates itself and revolves, i.e. travels around the internal gear, the travel path of the first point becomes a straight line and that of the second point becomes an ellipse. When the speed of rotation of the planetary gear around the internal gear is equal to the rotational speed of the internal gear, the travel path of the first point is a circle. Moreover, when the planetary gear rotates at a constant speed, by adjusting the speed of the internal gear, the travel path of the first point is a spiral and that of the second point is a near-hypocycloid.

Movement of those points is transmitted to a link mechanism. The link mechanism includes an X-ray tube and a film, both being supported facing each other with a specific region of an object in between, all being in a straight line. Said movement of each point is enlarged by the link mechanism and thereby the X-ray tube and the film are moved in accordance with a selected travel path. Such a link mechanism is suggested by U.S. Pat. Nos. 3,770,955, 2,353,145 and 2,167,116.

Figure 1:
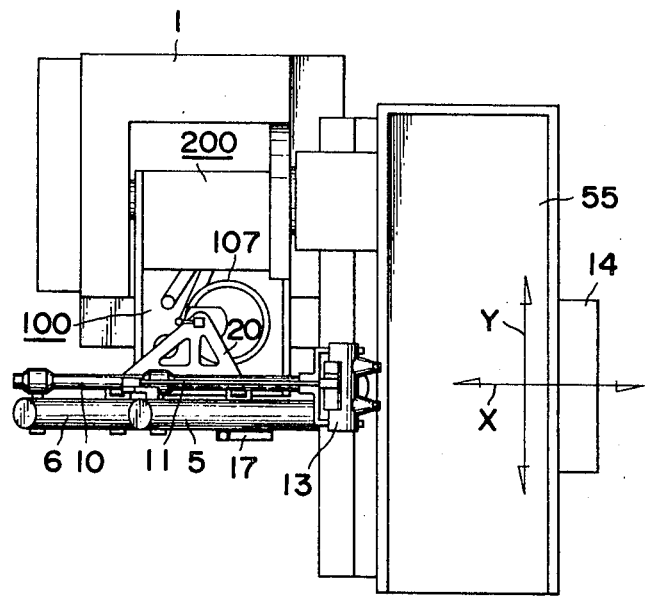
FIG. 1 is a plan view of the tomographic apparatus of the present invention.
Figure 2:
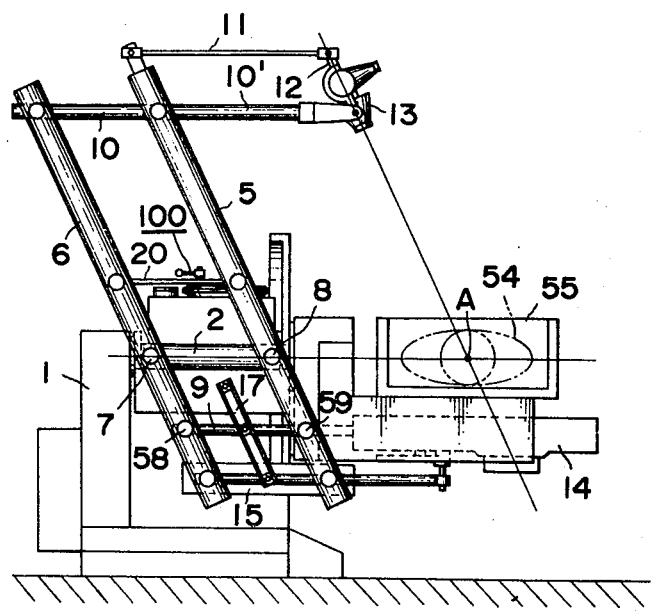
FIG. 2 is a front view of the same.

FIG. 1 and FIG. 2 show an embodiment of the tomographic apparatus of the present invention, showing a general assembly of the tomographic apparatus and details of the link mechanism, respectively. In the drawings, it will be noted that, on a base frame 1, there is supported a shaft 2 in bearing means in such a way that the shaft 2 is rotatable about its own axis in a direction Y which is shown by an arrow. Two main link arms 5 and 6 of link means are supported on pivots 7 and 8, respectively, on the ends of the shaft 2, so that these link arms 5 and 6 are rotatable in a direction perpendicular to the direction of rotation of the said shaft 2, or in other words, these main link arms 5 and 6 are rotatable in a direction of axis X. The directions of rotation of the shaft 2 and the link means are expressed as the directions of axis Y and axis X hereinafter as well as in the claims. Two bridge arms 9 and 10 are rotatably coupled to said main link arms 5 and 6. These four arms 9, 10, 5 and 6 constitute a parallelogram linkage which can make a swinging motion about the pivots 7 and 8 on the shaft 2 as well as about the shaft 2, in directions crossing at right angles or in other words in the directions of axes Y and X. Auxiliary arms 11 and 12 are operatively coupled to the upper end of the main link arm 5 and the end of the extension 10' of the bridge arm 10, respectively, to form another parallelogram linkage in this portion of the link means. The aforesaid arrangement provides link means which may be defined as a pantagraphically arranged linking mechanism which, as a whole, can be rotated in the directions of axis Y and axis X.

An X-ray tube 13 which serves as the X-ray source is secured to the auxiliary arm 12. On the other hand, a film holder 14 is secured to the foremost end of the extension of the bridge arm 9. A focus of the X-ray source 13, the center of the film mounted on the film holder 14 and a point A located on the extension of the longitudinal axis of the shaft 2 are arranged so that these three points will always lie on a rectilinear line irrespective of whatever angle of inclination is assumed by the link means as it is titled in the direction of axis Y and axis X.

The bridge arm 9 which supports the film holder 14 is rotatably supported by pivots 58 and 59. A balance load 15 is mounted on the lower ends of the main link arms 5 and 6 for balancing the forces existing on both sides of the shaft 2. An auxiliary arm 17 is coupled, at the upper end thereof by a ball joint, to the base frame 1 between the link arms 5 and 6 and also coupled to the bridge arm 9 by a pivot. This arm 17 is parallel with said link arms 5 and 6 so as to form a parallel linkage in a place perpendicular to FIG. 2. Because of this arrangement, it will be understood that when the link arms 5 and 6 are rotated in the direction of axis X about the pivots 7 and 8, the film holder 14 will carry out a movement, in parallel with and in correlation with the X-ray tube 13, in such a way that the center of the film mounted on the film holder 14, the focus of the X-ray source 13 and the point A on the extension of the longitudinal axis of the shaft 2 lie on a straight line. When the link arms 5 and 6 are rotated in the direction of axis Y about the shaft 2, on the other hand, the auxiliary arm 17 tilts about its pivotal point on the base frame 1 through an angle which is the same as that of the tilting of the link arms 5 and 6, so that the arm 17 rotates the bridge arm 9 to maintain the film holder 14 in a horizontal position in spite of the tilting of the link arms 5 and 6. At the same time, the center of the film mounted on the film holder 14 keeps the aforesaid correlationship with the X-ray tube 13 and the point A.

The point A represents a point lying on the tomographic plane of the object to be photographed by X-rays. Thus, it may be said that both the X-ray tube 13 and the film mounted on the film holder 14 are adapted to make spherical movements, respectively, about a point lying on the tomographic plane.

With the link mechanism having the aforesaid arrangement, let us now assume that a force is applied to the main link arm 5 in any arbitrary direction. Whereupon, the link arm 5 tilts in the direction in which the force is applied. Thus, the main link arm 5 is able to assume any arbitrary angle of inclination within the range of the maximum angle of inclination which is limited by the link mechanism as a whole and also by the base frame 1. Accordingly, the X-ray tube 13 and the film holder 14 are able to travel on any desired path of movement, starting at any arbitrary position on the faces of spheres formed about the point A, respectively. At the same time, the line which is formed by connecting the X-ray source 13, the point A located on the extension of the central longitudinal axis of the shaft 2 and the center of the film holder 14 will be a straight line in all cases.

The control means, fastened on the base frame 1, causes the link mechanism to move on a straight path in the axis X or Y, or in circular, elliptical, hypocycloidal or spiral paths. More particularly, the control means, as shown in FIGS. 3 to 11, comprises a drive mechanism 100 having an internal gear 107 and a planetary gear 104 in mesh therewith, and a control mechanism 200 for controlling the drive mechanism 100 and for adjusting the timing of X-ray irradiation. As stated before, in the drive mechanism 100, the internal gear 107 is in mesh with the planetary gear with a gear ratio of 2:1- that is, two self-rotations of the planetary gear 104 in mesh with the internal gear 107 causes one revolution of the planetary gear 104 around the internal gear 107.

The internal gear 107 has a pan-like portion which is integrally formed with periphery thereof. At the bottom of the said pan-like portion is a hollow shaft 134 supported in a bearing 131' in a casing 131. Therefore the internal gear 107 is rotated when the hollow shaft 134 rotates. The planetary gear 104 is rotatably supported by a pin 105 which is fixed to a crank plate 106. A shaft 108 passing through the hollow shaft 134 is supported in a bearing 132, has the crank plate 106 mounted on one end thereof. The pin 105 for the planetary gear 104 is fixed on the crank plate 106, so that when the shaft 108 rotates, the planetary gear 104, in mesh with the internal gear 107, rotates itself and revolves around the internal gear 107.

A gear 110 mounted on the shaft 108 for the planetary gear 104 is engaged with a gear 116 freely rotatably mounted on the shaft 128, and further associated with a gear 118 fixedly secured on a shaft 129 via a gear 117 rotatably secured coaxially with the gear 116. As a result, when the shaft 129 rotates, the shaft 108 starts to rotate without rotation of the shaft 128, and accordingly the planetary gear 104 rotates itself and revolves around the internal gear 107 in mesh therewith.

A gear 109 is fixedly secured on the hollow shaft 134 for the internal gear 107. The gear 109 is in mesh with a gear 115 fixedly secured on the shaft 128. In this case, the gear ratio of the gear 109 to the gear 115 equals to that of the gear 110 to the gear 116 in the gear train in respect to the planetary gear. The shaft 128 is operated together with the shaft 129 by electromagnetic clutches 112, 119 and 122. For instance, the gear 111 mounted for free rotation on the shaft 128 can be fixed thereon via the clutch 112. When the gear 111 is engaged with a gear 123 fixedly secured on the shaft 129, the rotation of the shaft 129 is transmitted to the shaft 128 via the clutch 112, with a speed-reducing ratio of 49/51. A gear 114 fixedly secured on the shaft 128 is meshed with a gear 120 freely rotatably mounted on the shaft 129. When the gear 120 is locked on the shaft 129 via the clutch 122, the shaft 128 rotates at a speed equal to the shaft 129. A gear 113 fixedly secured on the shaft 128 is enmeshed into with a gear 121 on shaft 129. The gear 121 is freely rotatably secured on the shaft 129 and also clamped thereon via the clutch 122. With this arrangement, the rotation of the shaft 129 is transmitted to the shaft 128 with a speed-reducing ratio of 1/4. Accordingly, while the shaft 108 for the planetary gear 104 makes a revolution, the rotation of the shaft 134 for the internal gear 107 is controlled by clutches: one revolution via the clutch 119, 1/4 revolution via the clutch 122 and 49/51 revolution via the clutch 112.

A casing 131 rotatably supports a shaft 241 on the top of which is mounted an electromagnetic brake 125 for locking the shaft 128. On the electromagnetic brake 125 is fixedly secured a gear 124 which is in mesh with a gear 121 freely rotatably mounted on the shaft 129. The electromagnetic brake 125 locks the shaft 128 at a normal condition, but releases it when switched on. In this case, locking of the shaft 241 means locking of the shaft 128. In other words, the electromagnetic brake 125 blocks the rotation of the internal gear 107 when switched off, but sets it free when switched on.

Figure 8:
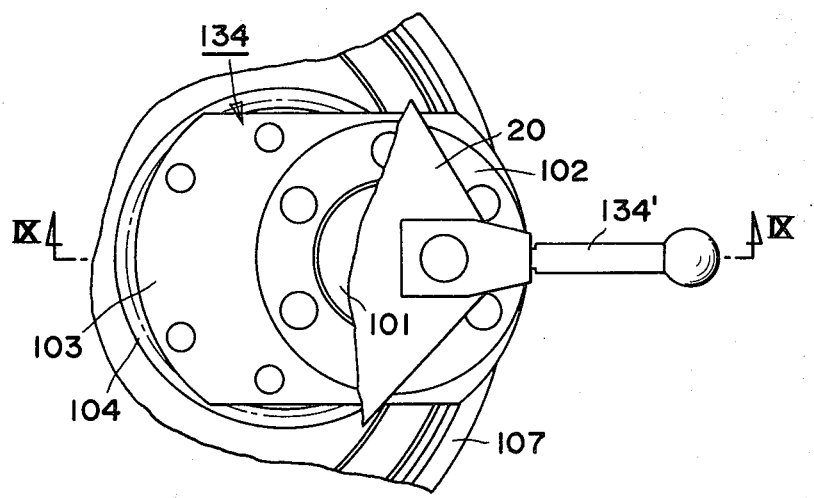
Figure 9:
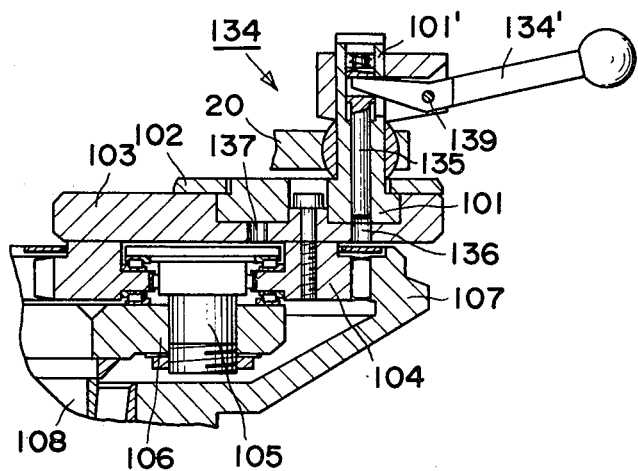
Figure 10:
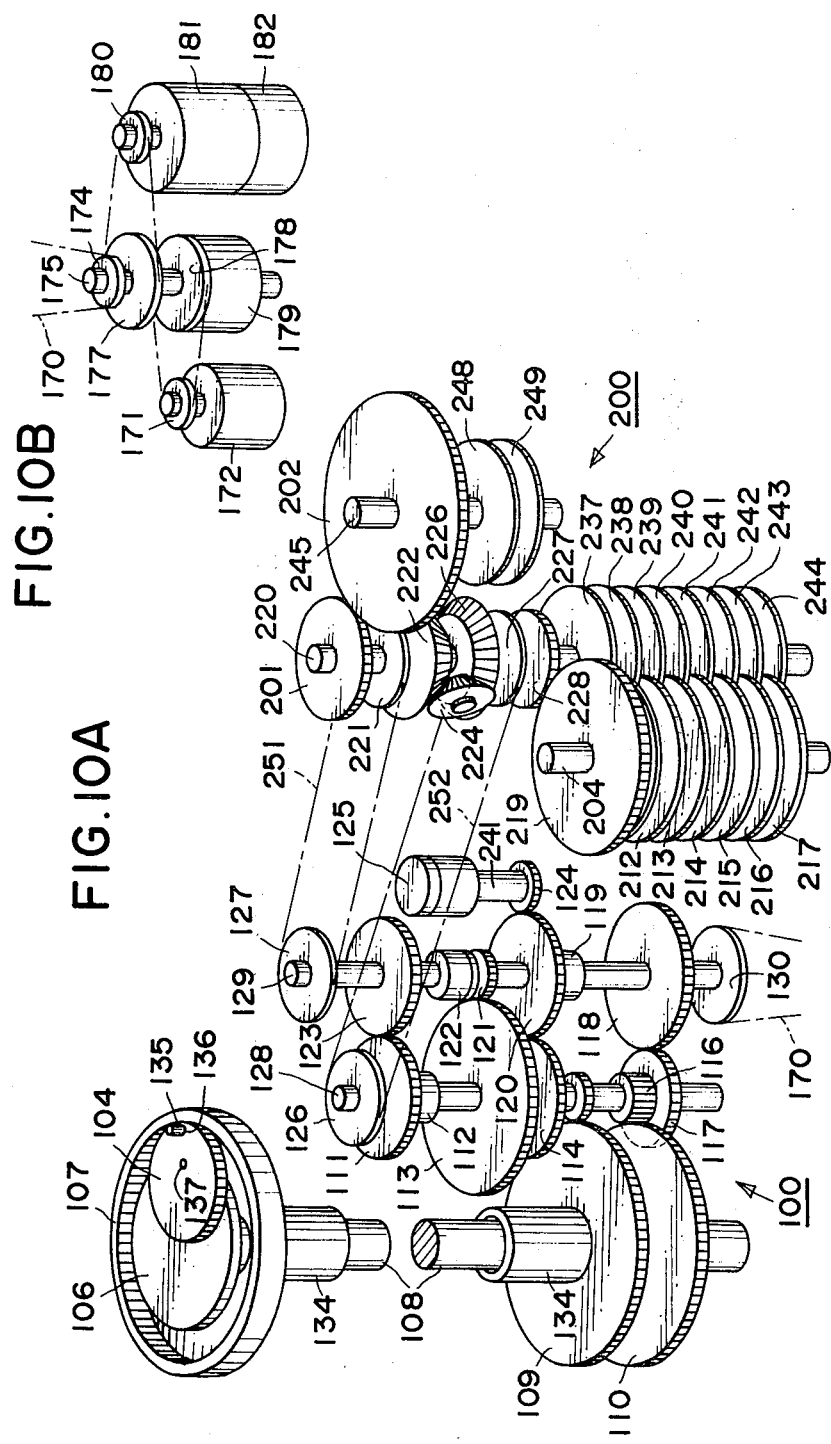

The drive mechanism having the aforesaid arrangement is connected to links 5 and 6 in the link mechanism through a triangular arm 20. The triangular arm 20 has two apexes connected to links 5 and 6 at points spaced from the shaft 2 and the pivots 7 and 8, respectively, by universal joints, and one apex is connected to a pin 135 which is inserted into the planetary gear 104 by a pin-setting means 134 as described later. FIG. 8 and FIG. 9 show details of the pin-setting means.

A plate 103 in which openings 136 and 137 are provided is attached to the planetary gear. The opening 136 is located on a pitch circle of the planetary gear, and the opening 137 is placed at a point which is 1/3 of the pitch circle diameter of the planetary gear 104. The rotating plate 101 is rotatably inserted into the plate 103, and secured by a plate 102. The rotation plate 101 has a column portion 101' wherein a pin 135 is built in so as to be freely slidable. The tip of the pin 135 is inserted into the opening 136 or 137 upon the rotation of the rotating plate 101. More specifically, the pin 135 is pressed by a coil spring 138 located at the opposite end thereof, in a direction to be urged into the opening 136 or 137. The midpoint of a lever 134' is rotatably supported extension of the column portion 101' by a pin 139.

The top of the lever 134' is engaged in a slot of the pin 135, passing through a slit formed in the column portion 101', so that the pin 135 is removed from the opening 136 or 137 when the lever 134' is pivoted, clockwise in FIG. 9, against the coil spring 138. The said triangular arm 20 linking the link mechanism and control means is coupled with the column portion 101' by a universal joint. When the pin 135 is inserted into the opening 136, as mentioned below, the path of movement of the pin 135 becomes a straight line, a circle and spiral. When the pin 135 is locked in the opening 137, the path of movement of the pin 135 is an ellipse and a hypocycloid. Movement of the pin 135, the said triangular arm 20.

Clutches 112, 119 and 122, and the brake 125 housed in the drive mechanism 100 are controlled by the control mechanism 200 further detects the start point of each movement and determines the timing of X-ray emission.

The control mechanism 200 has a frame 203 independent from the drive mechanism 100. A shaft 220 is supported in a bearing 250 attached to the frame 203. More particularly, the shaft 220 is provided with a differential gear mechanism comprising gears 222, 224 and 226. Gears 222 and 226 are rotatably secured on the shaft 220, and the gear 224 engaged therewith is also rotatably mounted on a shaft 225 which is an extension of a block 223 on the shaft 200. Sprockets 221 and 227, for grears 222 and 226 respectively, are provided on the shaft 200, which are connected to sprockets 127 and 126 mounted on shafts 129 and 128 in the drive mechanism through timing chains 252 and 251. Therefore, either when the shaft 129 rotates and the shaft 128 is locked, or when a difference is generated in the rotational speed of the shafts 129 and 128, the shaft 220 is rotated. When both shafts 128 and 129 rotate at the same speed, but in opposite directions, the shaft 220 is stopped.

In the control mechanism 200 there are shafts 245 and 204. The shaft 245 is supported by a bearing 253 mounted on the frame 203. The shafts 245 and 220 are coupled by gears 201 and 202 attached thereon, respectively. Therefore, when the shaft 220 rotates, the shaft 245 is driven. A shaft 204 is also rotatably supported by the frame 203. A gear 219 on the shaft 204 is coupled with the gear 226 and the sprocket 227 by a gear 228 on the shaft 220. Thus, when the shaft 220 rotates, the shaft 245 is driven.

Figure 6:
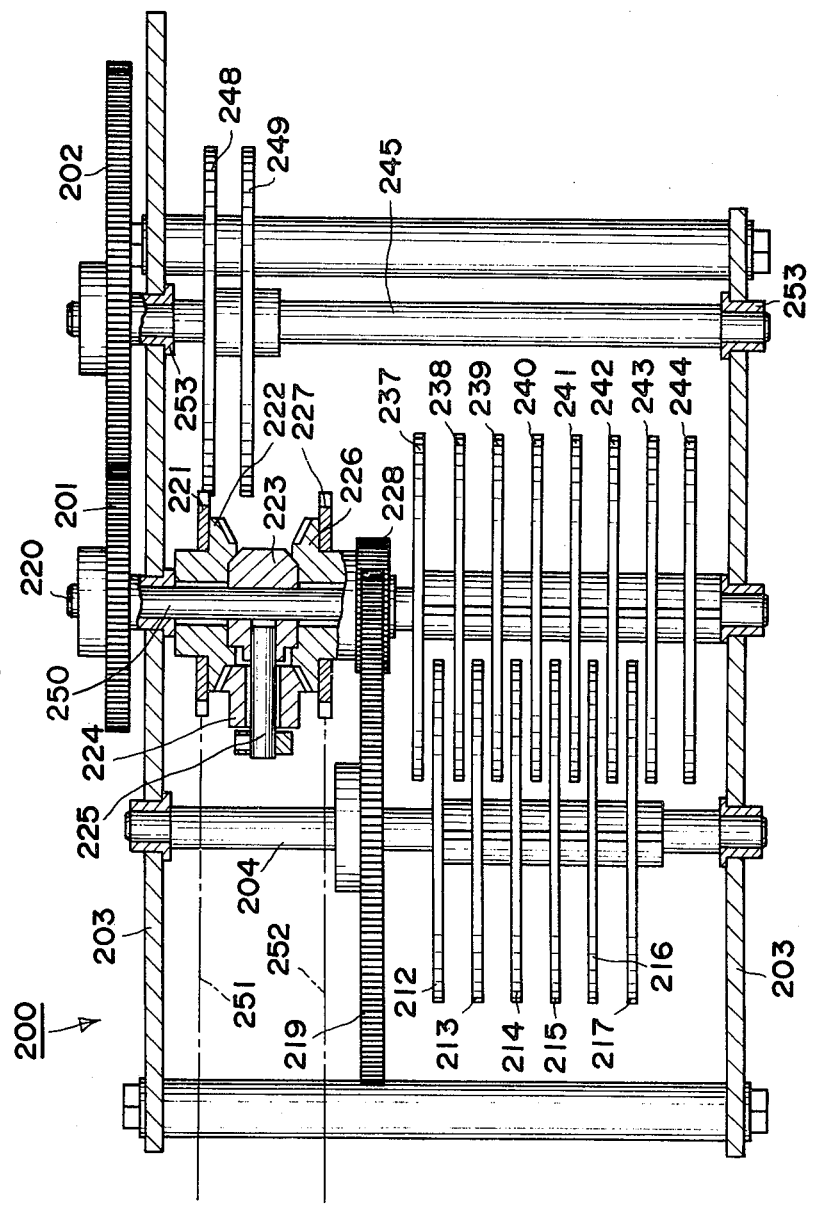
Figure 7:
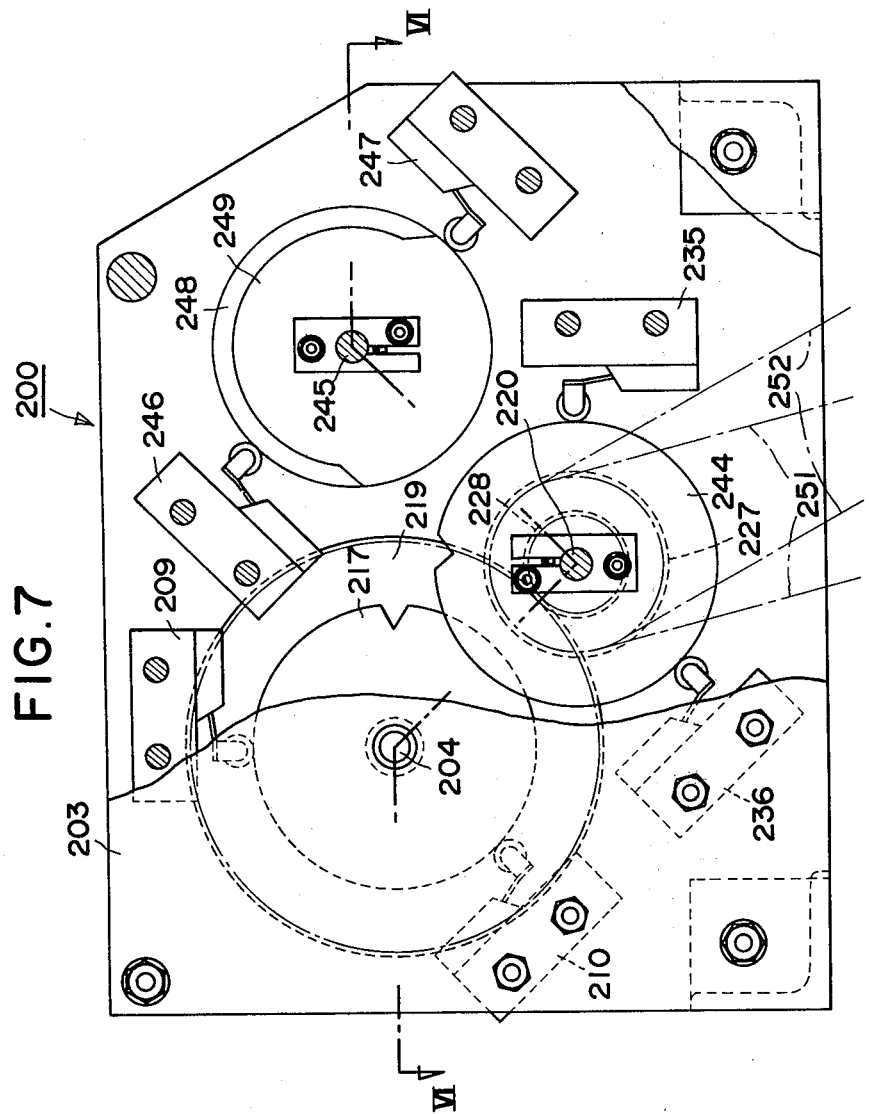
Figure 11:
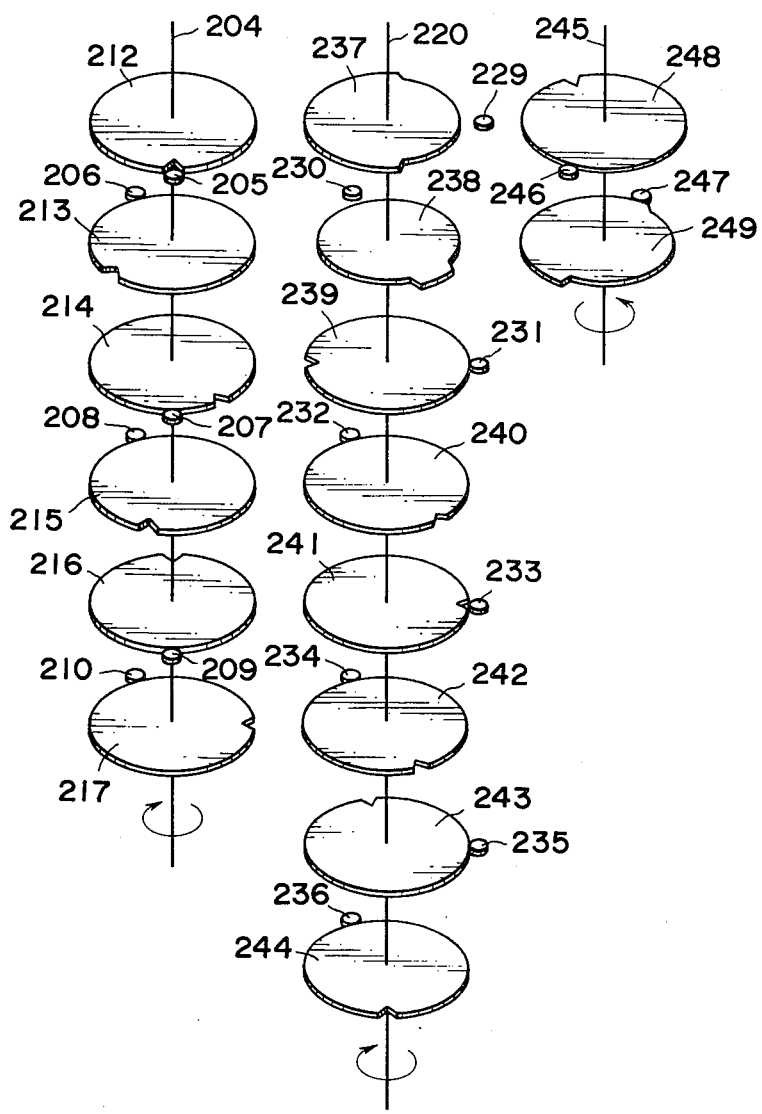

On each shaft a plurality of cam plates are fixed, and limit switches which are positioned around the cam plates are operated in accordance with the rotation of each shaft. As explained below, those cam plates and limit switches control the following operations. Cam plates 241 to 244 fixedly secured on the shaft 220 serve to detect the start points thereof, and limit switches 233 to 236 are located around the said cam plates. Cam plates 212 to 215 fixedly secured on the shaft 204 determine the start point in cooperation with the cam plates 241 to 244 on the shaft 220, and limit switches 205 to 208 are placed correspondingly to the said cam plates. On a shaft 245 a cam plate 249 is fixedly secured to determine the start point in co-operation with the cam plates 212 to 215 on the shaft 204 as well as the cam plates 241 to 244 on the shaft 220, and a limit switch 247 is provided for the cam plate 249. To determine the timing of X-ray irradiation, on the shaft 220 cam plates 237 to 239 are fixedly secured, on the shaft 204 cam plates 216 and 217 are fixedly secured, and on the shaft 245 a cam plate 248 is fixedly secured, and further limit switches 229, 231, 209, 210 and 246, which are all operated by the corresponding cam plates, are provided in contact with respective cam plates. Limit switches for the respective shafts, as illustrated in FIG. 6 and FIG. 11, are provided so that even numerals are located on one rod while odd numerals are placed on the other rod for reducing the mounting space and easing attachment of limit switches. More specifically, limit switches are secured on two rods which are separately positioned between two frames 203 and 204.

The drive mechanism 100 and control mechanism 200, as described above, are driven by rotating the shaft 129 incorporated in the drive mechanism 100. A shaft 175 is provided with a pulley 174 which is connected to a pulley 130 on the shaft 129 by a belt 170. The shaft 175 is also provided with pulleys 177 and 178. The pulley 177, which is linked with a pulley 180 of a motor 181 by a belt, causes the shaft 129 to rotate when the motor 181 starts. The motor 181 is provided with an electromagnetic brake 182. The pulley 178 is linked with a pulley 171 of a motor 172 by a belt and is locked to the shaft 175 only when the clutch 179 is actuated and at the same time the rotation of the motor 172 is transmitted to the shaft 129. Operation of the tomographic apparatus of the present invention having the aforesaid arrangement will be described hereinafter.

When the present tomographic apparatus is operated, and the pin 135 is clamped into the opening 136 by means of the lever 134, a path-selecting switch is actuated and a preliminary operating switch is operated, so that the X-ray tube and the film is shifted to the start point in accordance with a selected path of movement. After that, when an X-ray photographic switch is actuated, the X-ray tube and the film travel in a selected path of movement, and X-rays are emitted for a specific time. Now all operations are completed.

Figure 12A:
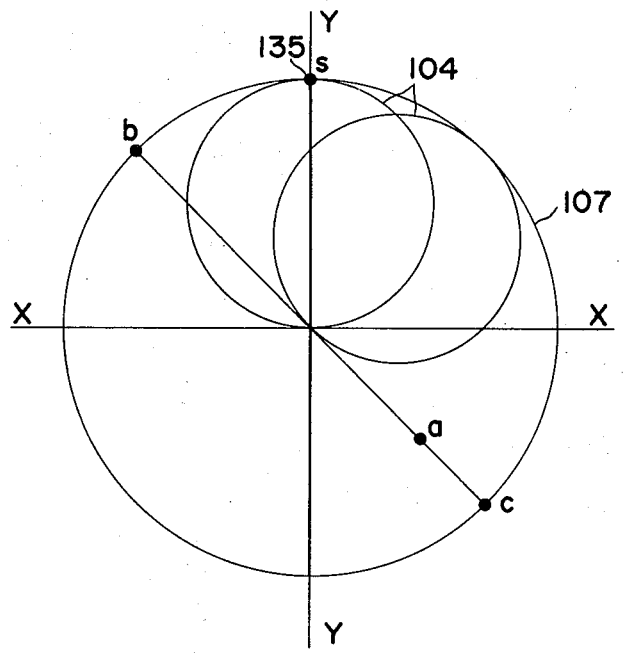
FIGS. 12A to 12G are diagrams explanatory, showing how the control means in the tomographic apparatus according to the present invention effects movement along a straight line, large circle small circles, an ellipse, a near-hypocycloid, twin spirals, and triple spirals, respectively.

The straight movement in the axis Y is carried out as follows. When the preliminary operating switch is actuated, the motor 172 starts, and at the same time the pulley 178 is locked to the shaft 175 by the clutch 179, so that the rotation of the motor 172 is transmitted to the shaft 108 for the planetary gear 104 via the shaft 129. At this time, since the movement of the internal gear 107 is blocked by the brake 125, the planetary gear, in mesh with the internal gear 107, rotates itself and travels around the internal gear 107. As a result, the pin 135 locked into the opening 136 on a pitch circle of the planetary gear, as shown in FIG. 12A, travels along a straight line passing through the center of the internal gear 107 from a point *a* which corresponds to a random position at which the pin has been left as a result of the position of the apparatus immediately before the X-ray tube and the film start to move. This movement, via the triangular arm 20, is transmitted to the link mechanism in which the movement is enlarged, which in turn causes the X-ray tube and the film to move in a straight path.

On the other hand, the rotation of the shaft 129 causes only the gear 222 for the differential gear mechanism in the control mechanism 200 to rotate. In this case, the differential gear 266 of the gear mechanism is stopped because the shaft 128 is clamped by the brake 125. Accordingly, the shaft 220 is caused to rotate. The rotation of the shaft 220 causes the shaft 245 to rotate via gears 201 and 202.

When the pin 135 reaches a point c on a circle corresponding to a pitch circle of the internal gear 100, the limit switch 233 contacting the cam plate 241 for the shaft 220 is operated. Since the shaft 108 still continues to rotate, the pin 135 is shifted to a point *b* on the opposite side in the same straight path. When the pin 135 arrives at the point *b*, the limit switch is switched on; by the cam plate 241. The cam plate 249 and the limit switch 247 of the shaft 245 are arranged in such a manner that when the pin 135 reaches the point *b* which is designated as the preliminary-operating position as between both extreme ends b and c, the limit switch 247 and the cam plate 249 actuate the brake 125 and clutch 119 in the drive mechanism 100 which are actuated only when both switches 233 and 247 operate.

Actuation of the brake 125 causes the internal gear 107 to rotate freely, and the clutch 119 locks the gear 120 to the shaft 129 in order to rotate the hollow shaft 134 by the shaft 128, thereby rotating the internal gear 107 at the speed same as that of the planetary gear 104. As a result, the pin 135 travels in a circle corresponding to the pitch circle of the internal gear - that is, in a direction from the point *b* to a start point s for y-axis movement in FIG. 12A. Furthermore, when the shaft 128 rotates, gears 222 and 226 in the differential gear mechanism in the control mechanism 200 are rotated at the same speed, and the shaft 220 is stopped. However, when the gear 226 rotates, the shaft 204 is rotated via gears 228 and 219. Moreover, when the pin 135 arrives at the start point s on the pitch circle, the limit switch 205 is actuated by the cam plate 212 on the shaft 204.

Only when the limit switches 205, 233 and 247 are all actuated as stated above, are the motor 172 and the clutch 179 switched off, and the brake 125 is switched off, whereby the rotation of the internal gear 107 and the planetary gear 104 is blocked, and the pin 135 is stopped at the start point s. The X-ray tube and the film, of course, move in accordance with the movement of the pin 135. FIG. 11 shows the spaced relationship among all cams in this state.

In case of movement of the X-ray tube and the film in the Y-direction, the X-ray tube and the film are first restored to the start point *s* and stopped there as described before immediately above. When an operator actuates a photographing switch, the X-ray tube and the film are moved in a selected Y-direction, starting at point S in FIG. 12A, X-rays are emitted, and thereafter the entire mechanism is stopped. More specifically, by actuating the photographing switch, the motor 181 starts, the shaft 129 is rotated thereby, and the shaft 108 of the planetary gear 104 rotates. In this case, the internal gear 107 is clamped since the brake 125 is switched off. Thus, the planetary gear rotates itself and revolves around the internal gear in mesh therewith, and the pin 135 moves in a straight path. The movement of the pin 135 is enlarged by the link mechanism, which is turn causes the X-ray tube and the film to travel in the Y-direction. On the other hand, the rotation of the shaft 129 is transmitted to the shaft 220 in the control mechanism 200. By choosing a cam plate 237 or 288 on the shaft 220, two times of X-ray irradiation can be selected. For example, if the cam plate 237 and its related limit switch 229 are chosen, the cam plate 237 rotates in accordance with the rotation of the planetary gear 104, and X-rays are emitted by actuating the limit switch 239 when the X-ray tube and the film arrive at the fixed position. At this time, the motor 181 is turned off and locked by the brake 182. Now the movement in the Y-direction is completed.

In case of movement in the X-direction, similarly to the movement in the Y-direction, the arrival of the pin 135 at the start point in the X-direction is detected by the cam 213 and the limit switch 206, after movement from the position at the end of the preceding operation, as a result of; operating the preliminary switch and the travel pass selecting switch. Thereafter, by actuating the photographing switch, only the planetary gear 104, in mesh with the internal gear 107, rotates itself and revolves around the internal gear 107, causing the pin 135 to travel in a straight path, which in turn moves the X-ray tube and the film in the X-direction by the link mechanism. In this movement, the timing of the X-ray irradiation is determined by either the set consisting of the cam plate 237 and limit switch 229 or the set consisting of the cam plate 238 and limit switch 230. Upon completion of the X-ray emission, the movement in the X-direction is over.

Figure 12B:
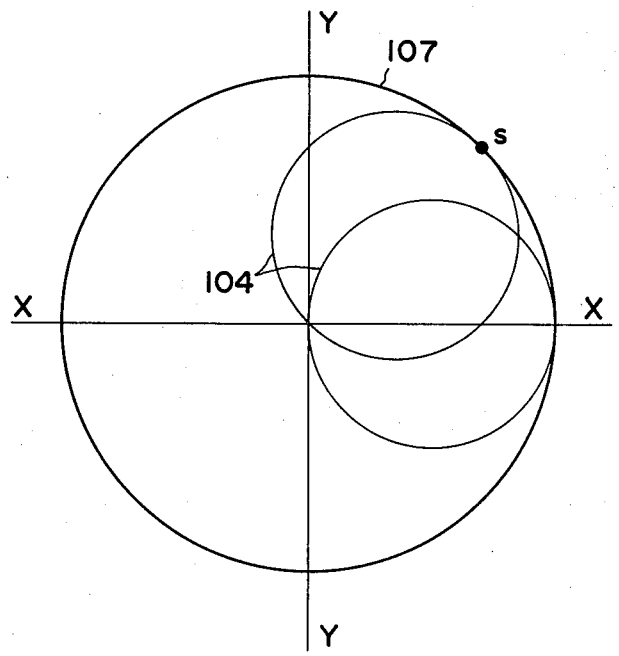
Figure 12C:
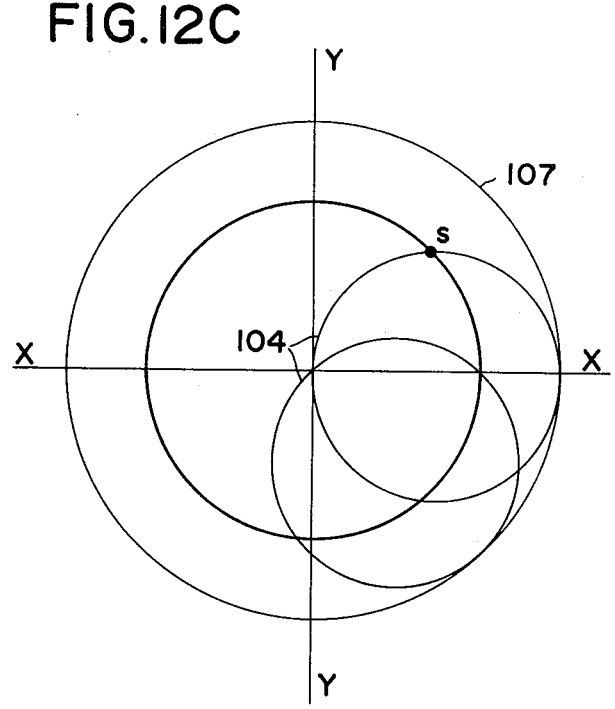
Figure 12D:
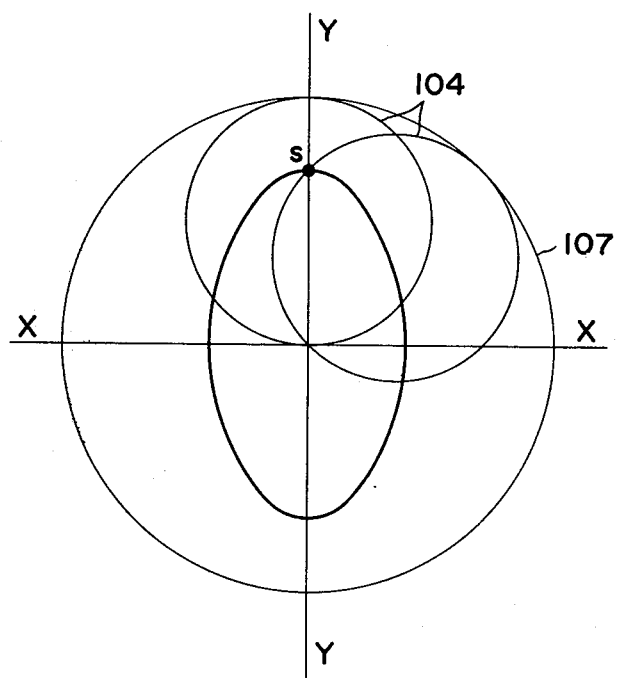

To move the X-ray tube and the film in an elliptical path, the pin 135 in the drive mechanism is locked into the opening 137 by means of the lever 134. The preliminary operation wherein the pin 135 is set at the start point s is carried out in a manner similar to the straight movement as explained before. At first, with the cam plate 241 and the limit switch 233, the position of the pin 135 on a circle having a half of a major axis of the predetermined elliptical path as a radius is detected. Second, with the cam plate 212 and the limit switch 205, the pin 135, as shown in FIG. 12D, is shifted to a start point s. Now all preliminary operations are completed.

When the photographing switch is actuated, the brake 125 in the drive mechanism 100 is locked, releasing all clutches 119, 122 and 112. Thus, whereas the rotation of the motor is transmitted to only the shaft 108, the planetary gear 104, in mesh with the internal gear 107 being locked, rotates itself and travels around the internal gear 107. Meanwhile, the pin 135 moves in the elliptical path, and simultaneously the X-ray tube and the film trace an elliptical path. The X-ray irradiation is made at 90° ahead of the start point s by the cam plate 248 and the switch 246, and stopped by actuating the switch 246 again. At the time when the X-ray irradiation is stopped, the motor 181 stops and the brake 182 is actuated.

In the circular movement of the X-ray tube and the film, there are two circular paths: a maximum circle that the pin 136 traces in the pitch circle of the internal gear: and a smaller circle. The maximum circle can be obtained by locking the pin 135 into the opening 136. The preliminary operation, similarly to the straight-movement, is such that the cam plate 241 and the limit switch 233 transfers the pin 135 to a start point in the pitch circle of the internal gear - that is, shifting the pin 135 to the start point s in FIG. 12B. When the photographing switch is operated, the brake 125 in the drive mechanism 100 is released, and in turn the gear 120 is locked to the shaft 129 by the clutch 119. When the motor starts, the internal gear 107 and the planetary gear 104 both rotate in the same direction and at the same speed. In this case, whereas the relative speed becomes zero, the pin 135 travels in a circular path corresponding to the pitch circle of the internal gear 107 starting at the start point s, which in turn lets the X-ray tube and the film move in a circular path. The X-ray irradiation is controlled by the cam plate 216 and the switch 209. That is, the X-ray irradiation begins when the cam plate 239 arrives at a point where it is 135° ahead of the start point, and the X-ray irradiation stops when the cam plate 239 returns to the said point again. At this time, all operations are over.

In movement in a smaller circular path, the pin 135 is also locked into the opening 136. In this movement, as a preliminary operation, the pin 135 is radially shifted to a point in a predetermined circle by rotating gear 104 relative to gear 107 by the cam plate 242 and the limit switch 234, and further shifted to a start point s by the cam plate 214 and the limit switch 207 as shown in FIG. 12C, and thereafter maintaining the said radially spaced relationship. In this case, the photographing operation is identical with that in the case of the maximum circle.

Figure 12E:
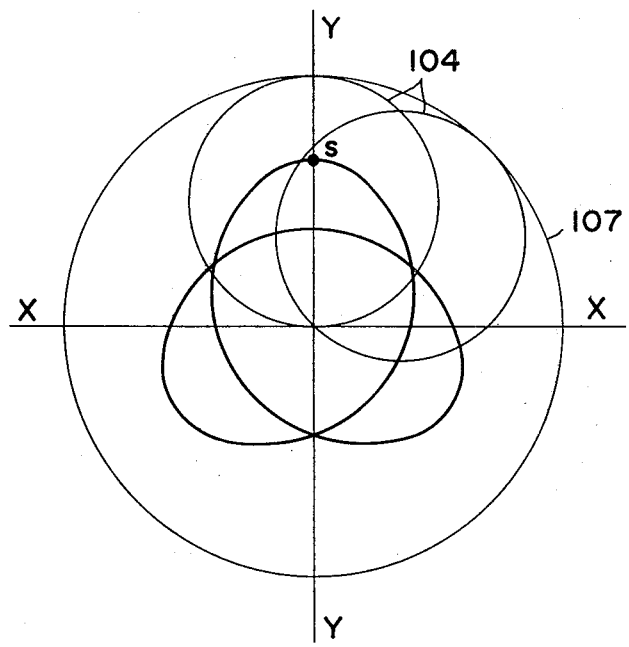

In movement of the X-ray tube and the film in a nearhypocycloid, the pin 135, as for elliptical movement, is locked into the opening 137. A preliminary operation, similar to the elliptical movement, is conducted so that the pin 135 is positioned at a start point s by means of the cam plate 241 and the limit switch 233, and the cam plate 212 and the limit switch 205, as shown in FIG. 12E. When the photographic switch is actuated, the motor 181 starts, the brake is released, and the clutch 122 is actuated. As a result, the internal gear 107 rotates at 1/4 the speed of the shaft 108 of the planetary gear 104 and in the same direction as the shaft 108. Thus, while the shaft 108 makes two revolutions, and the planetary gear 104 makes two revolutions and revolves around the internal gear 107 simultaneously, the internal gear 107 makes 1/4 revolution, causing the pin 135 to trace a near-hypocycloid. The X-ray emission starts when the cam plate 239 rotates 180° ahead of a start point by actuating the limit switch 231, and stops when the cam plate 239 is returned to the start point by switching off the switch 231. Now all operations are completed.

Figure 12F:
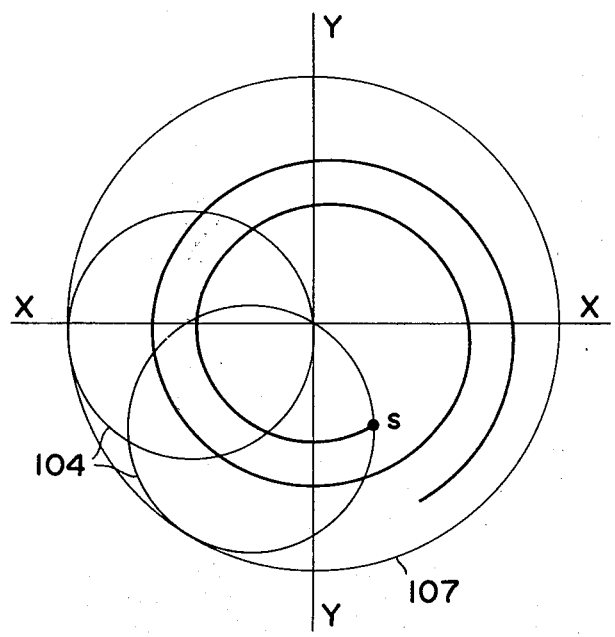
Figure 12G:
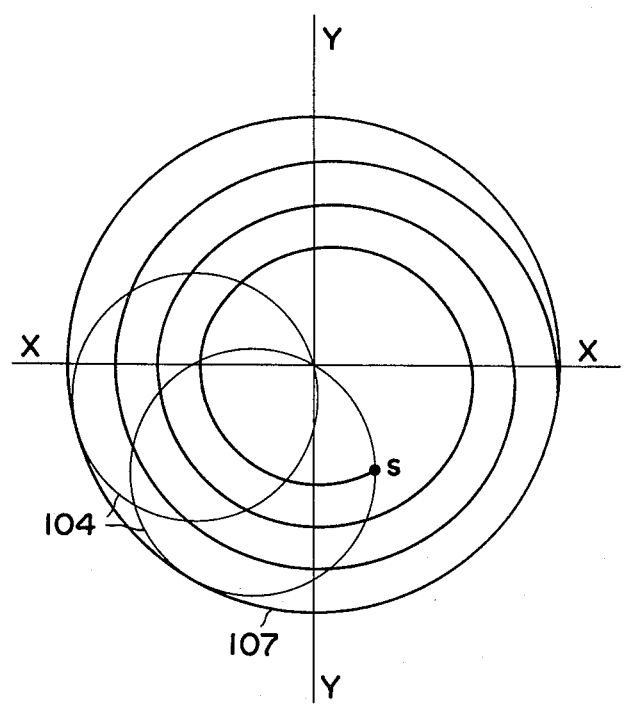

In spiral movement, the pin 135 is locked into the opening 136. A preliminary operation, as well as the straight movement, is performed so that radial movement of the pin 135 is controlled by the cam plate 243 and the limit switch 235, and the pin 135 is transferred to a start point s by the cam plate 215 and the limit switch 208, as illustrated in FIG. 12F and FIG. 12G. When the photographing switch is actuated, the motor 181 starts, the brake 125 is released, and the gear 111 is locked to the shaft 128 by the clutch 112. As a result, the internal gear 107 rotates at 45/51 speed of the shaft 108 of the planetary gear 104 and in the same direction as the shaft 108: when the shaft 108 makes two turns, the pin 135 traces two spiral turns. The X-ray irradiation is controlled by the cam plate 217 and the limit switch 210. When the x-ray irradiation is completed, all operations are also over. Three spiral turns, similar to the two spiral turns, are achieved by turning the shaft 108 three revolutions, as shown in FIG. 12G. In spiral and hypocycloidal movement, the length of X-ray emission is controlled by counting the number of revolutions of the cam plate.

What is claimed is:
1. A tomographic apparatus for taking tomographs comprising:
   linking means for swingably supporting an X-ray tube and a film in such a way that the X-ray tube and the film are always positioned in a straight line with an image point of an object located therebetween; and
   control means for imparting to said link means swinging movement in predetermined paths;
   said control means having a drive mechanism coupled with said link means and also having a control mechanism for operating said drive mechanism in accordance with a selected trace of travel, said drive mechanism having a rotatable internal gear and a planetary gear rotating about its own axis and revolving around said internal gear in mesh therewith, the diameter of the pitch circle of said internal gear being twice as large as the diameter of the pitch circle of said planetary gear, a pin coupled to said link means and which can be fixed at a first point on the pitch circle of said planetary gear or at a second point located on said planetary gear and spaced from the pitch circle of said planetary gear, said pin also being at a position spaced from the center of swinging movement of said link mechanism and being movable along predetermined paths by the rotation of said internal gear and said planetary gear;
   said control mechanism having: an X-ray irradiation timing control means which controls the time of operation of said X-ray tube while said pin moves in selected paths of movement; and a preliminary-position-detecting means coupled to said drive mechanism for shifting said pin to a starting position in accordance with each selected path of movement, said preliminary-position-detecting means having: a radius-detecting means for shifting said pin by rotating only said planetary gear to a specific position on a circle defined by a radius predetermined for a specific path of movement and a phase-detecting means for shifting said pin further to a starting position of said path of movement by rotating both said planetary gear and said internal gear.

2. A tomographic apparatus according to claim 1 in which said second point is at a position at 1/3 of the pitch circle diameter of said planetary gear, and said drive mechanism has drive means for driving said internal gear and said planetary gear independently, a drive for said internal gear in said drive means having: a speed-changing means for changing the speed ratio of said internal gear to said planetary gear among the ratios 1/1, 1/4 and 49/51; and a brake means for blocking the rotation of said internal gear arbitrarily, said radius-detecting means having a rotatable shaft and a plurality of cam means rotating at the same speed as said rotatable shaft, said cam means having: cam plates corresponding to respective straight, circular, elliptical, near-hypocycloidal and spiral paths; and switches engageable with said cams and each operating at each revolution of each of said cam plates, at least one of said switches being coupled to said brake means, whereby said cam plates actuate related switches for blocking rotation of said internal gear by means of said brake means when said pin reaches said specific position on a circle defined by a radius predetermined for a specific path of movement, said control mechanism having a radius increase/decrease detecting means which is provided with a shaft rotating at half the speed of said shaft for said radius-detecting means and having a cam means rotating the same speed as said shaft in order to actuate said brake means for blocking the rotation of said internal gear when said pin reaches said specific position on said circle defined by the radius predetermined for the specific path of movement, said phase-detecting means having a rotatable shaft and a plurality of further cam means rotating at a speed equal to said rotatable shaft, said further cam means having: further cams corresponding to respective straight, circular, elliptical, hypocycloidal and spiral paths, and further switches engaged with said cams and each being actuated on each revolution of each of said cams, said switches being coupled to said control means, whereby said drive mechanism is stopped when said pin arrives at said starting point in said path of movement, after being moved along said circle; and said control mechanism further having a differential gear means which is coupled to said shaft for said radius-detecting means for rotating said shaft either when said planetary gear rotates and said internal gear is stopped, or when a difference is generated in the rotational speed of said planetary gear and said internal gear, and coupled to said shaft for said phase-detecting means for rotating said last-mentioned shaft only when both said planetary gear and said internal gear rotate.

3. A tomographic apparatus according to claim 2 in which said X-ray irradiation timing means has: a plurality of X-ray cams on each of the respective shafts in said radius-detecting means; phase-detecting means and radius increase/decrease detecting means and rotatable at the speeds of said shafts; and switches engaged with said cams and coupled to said X-ray tube and each actuated at each revolution of each of said X-ray cams, thereby controlling the start and stop of the X-ray irradiation.

4. A tomographic apparatus according to claim 3 in which said cams are fixedly secured on the related shafts at proper rotational positions, and said apparatus further having rods parallel to said shafts on which said switches corresponding to said cams are fixedly secured.

5. A tomographic apparatus according to claim 2 in which said drive mechanism has a pin-setting means, said pin-setting means being fixedly secured to said planetary gear and comprising: a plate having openings therein at points corresponding to said pin-setting positions; a rotating plate rotatably secured to said plate, having a center of rotation corresponding to between the positions of said opening and an opening on a radius thereof corresponding with the positions of said openings; a pin freely slidable in said opening in said rotating plate; a spring engaging said pin and urging it with said opening in said rotating plate; a lever rotatably supported by said rotating plate and one end being engaged with said pin; and an arm having one end attached to said pin for universal pivotal movement and having the opposite end coupled with said link mechanism for universal pivotal movement.

6. A tomographic apparatus according to claim 2 in which said drive mechanism has drive means for said planetary gear comprising: a rotatable shaft; a gear train coupled between said rotatable shaft and said planetary gear which transmits rotation of said rotatable shaft to said internal gear, and said speed-changing means changes speed to transmit rotation of said shaft of drive means for planetary gear to said shaft of said drive means for internal gear.

7. A tomographic apparatus according to claim 6 in which said differential gear means in said control mechanism has two bevel gears rotatably secured on said shaft of said radius-detecting means, and a further bevel gear engaged with said two bevel gears, said first-mentioned bevel gears being respectively engaged with said shaft of said rotating means for said internal gear and said shaft of said rotating means for said planetary gear.

8. A tomographic apparatus according to claim 6 in which said drive means has: a drive shaft connected to said shaft of said drive means for said planetary gear; a first motor engaged with said drive shaft; a transmission means for connecting a motor to and disconnecting it from said drive shaft; and a second motor coupled with said transmission means, said transmission means being connected to the switch operated by said cam in said radius-detecting means for disconnecting said second motor from said drive shaft, and said first motor being coupled to a switch which is associated with said cam in X-ray irradiation timing means for being stopped thereby.

* * * * *